United States Patent
Van Liew et al.

(10) Patent No.: US 6,503,516 B1
(45) Date of Patent: Jan. 7, 2003

(54) MAKE-UP COMPOSITION CONTAINING A BLEND OF WAXES

(75) Inventors: Terry Van Liew, Cranford, NJ (US); Olga Alonzo, Passaic Park, NJ (US); Michael Smith, Branchburg, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/434,130

(22) Filed: Nov. 5, 1999

Related U.S. Application Data

(60) Provisional application No. 60/107,345, filed on Nov. 6, 1998.

(51) Int. Cl.[7] .............................. A61K 7/00; A61K 7/42; A61K 7/021; A61K 7/025
(52) U.S. Cl. .......................... 424/401; 424/59; 424/63; 424/64; 424/400; 424/DIG. 5
(58) Field of Search ................................. 424/400, 401, 424/59, 63, 64, DIG. 5

(56) References Cited

U.S. PATENT DOCUMENTS

| | | |
|---|---|---|
| 4,014,995 A | 3/1977 | Juliano et al. |
| 4,405,641 A | 9/1983 | Seibert |
| 5,225,186 A | 7/1993 | Castrogiovanni et al. |
| 5,486,352 A * | 1/1996 | Guerrero ..................... 424/59 |
| 5,837,223 A * | 11/1998 | Barone et al. ................ 424/64 |
| 6,042,815 A * | 3/2000 | Kellner et al. ................ 424/63 |

FOREIGN PATENT DOCUMENTS

| | | |
|---|---|---|
| EP | 0 666 072 A2 | 8/1995 |
| JP | 358092605 * | 6/1983 |
| WO | WO 94/06401 | 3/1994 |
| WO | WO 95/11000 | 4/1995 |

* cited by examiner

*Primary Examiner*—Jose' C. Dees
*Assistant Examiner*—Marina Lamm
(74) *Attorney, Agent, or Firm*—Finnegan, Henderson, Farabow, Garrett & Dunner, L.L.P.

(57) ABSTRACT

A composition which can be molded in the form of a stick or hot-poured, comprising
- at least one wax having a melting point of greater than 95° C. and a penetration of from 1 to 7.5 mm, and
- at least one organically modified beeswax having a penetration of greater than 7.5 mm,
- wherein the waxes are present in a combined amount sufficient to provide stability and a creamy texture to a molded stick or to a product resulting from hot-pouring, and a process for caring for and/or making-up the eyes, lips, or skin using this composition.

19 Claims, No Drawings

MAKE-UP COMPOSITION CONTAINING A BLEND OF WAXES

This application claims the benefit of U.S. Provisional Application No. 60/107,345, filed Nov. 6, 1998.

The present invention relates to a cosmetic composition in the form of a stick or hot-poured product which can be used for caring for and/or for making up the human face, in particular, the skin, eyelids, or lips.

Cosmetic compositions in stick form, such as lipsticks, eyeshadows and eyeliners, and stick foundations or concealers generally contain fatty substances, such as oils and waxes, to help form a composition which can be shaped into a stick. The sticks are traditionally made by pouring the components into a mold to form the desired shape. The use of conventional waxes in cosmetic sticks often results in an undesirable waxy or "candlestick" texture, particularly if a large amount of wax is added in order to try to achieve a solid stick form.

Now, the inventors have discovered, unexpectedly and surprisingly, that the mixture of a unique combination of waxes, when used in a composition in gelled form, results in a stable, creamy, and easy to apply makeup stick. The gelled effect gives the inventive stick a much creamier texture than the conventional poured stick. The makeup product of the invention provides a single product which can be used as a makeup, a concealer, and, after blending, gives a powder feel. The invention may also be used as an eyeshadow, an eyeliner, a blush, or a lip composition. In addition, the product of the invention, instead of being molded in the form of a stick, may also be hot-poured.

Specifically, the composition of the invention comprises:
at least one wax having a melting point of greater than 95° C. and a penetration of from 1 to 7.5 mm, and
at least one organically modified beeswax having a penetration of greater than 7.5 mm.

The waxes are present in a combined amount sufficient to impart the above-described stability and creamy texture to the makeup product of the invention. In one embodiment, the composition of the invention is anhydrous.

Several of the waxes present in the composition of the invention are defined by their penetration value. The penetration test used by the inventors is set forth in A. H. Warth, *The Chemistry and Technology of Waxes*, Reinhold Publ. Corp, N.Y., 1947, and is a standard test for hardness of waxes. The test measures the depth in millimeters that a standard needle weighing 100 g penetrates the surface of a wax when measured for 5 seconds at 25° C.

The waxes having a melting point of greater than 95° C. and a penetration of from 1 to 7.5 mm which are useful in the present invention include, but are not limited to, polyethylene waxes having a weight-average molecular weight ranging from 350 to 900; candelilla wax; carnauba wax; and organically modified carnauba waxes. In one embodiment, the useful polyethylene waxes have a weight-average molecular weight ranging from 400 to 500. Organically modified carnauba waxes useful in the present invention include, but are not limited to, carnauba waxes modified with polyethylene glycols (PEG) ranging from PEG-4 to PEG-20 and with polypropylene glycols (PPG) ranging from PPG-9 to PPG-26. In one embodiment, the wax having a melting point of greater than 95° C. and a penetration of from 1 to 7.5 mm is PEG-12 carnauba wax. The at least one wax having a melting point of greater than 95° C. and a penetration of from 1 to 7.5 mm is present in the inventive composition in an amount ranging from greater than 0% to about 12%, relative to the total weight of the composition.

Organically modified beeswaxes having a penetration of greater than 7.5 mm useful in the present invention include, but are not limited to, PEG-8 beeswax, polyglycerol-3 beeswax, and siliconized beeswax such as dimethicone copolyol beeswax. In one embodiment, the organically modified beeswax is dimethicone copolyol beeswax. The organically modified beeswax having a penetration of greater than 7.5 mm is present in the inventive composition in an amount ranging from greater than 0% to about 7%, relative to the total weight of the composition.

The composition of the invention may further include at least one additional wax chosen from synthetic waxes having a penetration of greater than 7.5 mm and natural waxes which are non-modified and have a penetration of from 11 to 23 mm. These wax(es) are present in the inventive composition in an amount of greater than 0% to about 7% relative to the total weight of the composition.

Synthetic waxes useful in the present invention include, but are not limited to, microcrystalline, ozokerite, ceresine, hydrogenated jojoba, and paraffin waxes having a penetration of greater than 7.5 mm. Non-modified natural waxes that may be used include, but are not limited to, non-modified beeswax having a penetration of from 11 to 23 mm.

The composition of the invention may also include a skin-conditioning emollient. The emollient functions as a softener to help the makeup product of the invention give a desirable feel on the skin. Useful emollients include, but are not limited to fatty bodies liquid at ambient temperature, such as esters, mineral oils, animal oils, vegetable oil, synthetic oils, and silicone oils.

Examples of useful esters include, but are not limited to, isononyl isononanoate, octyl palmitate, cetyl lactate, pentaerythrityl tetraoctanoate, tridecyl octanoate, tridecyl behenate, isopropyl jojobate and jojoba alcohols, butyloctyl salicylate, polyglyceryl-3 diisostearate, squalane, tridecyl trimellitate, tridecyl stearate, and neopentylglycol dicaprylate/dicaprate. In one embodiment of the invention, the esters are chosen from isononyl isononanoate, a light ester which adds to the initial feel of the inventive composition on the skin, and pentaerythrityl tetraoctanoate, an ester which helps to cushion after the makeup is blended into the skin.

Examples of useful oils include, but are not limited to, petrolatum oil, liquid lanolin, arara oil, sesame oil, macadamia oil, jojoba oil, silicone oils such as phenyl trimethicone and dimethicone, and synthetic triglycerides such as capric caprylic triglyceride and hydrogenated cocoglycerides.

Another useful emollient is an oleosoluble synthetic polymer whose use in cosmetic compositions is known. Representative oleosoluble synthetic polymers include polyvinylpyrrolidone/hexadecene or PVP/eicosene copolymers, such as products sold by GAF Corp. under the tradenames GANEX V-216 and GANEX V-220.

Other useful skin conditioning emollients are listed in the International Cosmetic Ingredient Dictionary and Handbook, $7^{th}$ Edition, Vol. 2, pp. 1656–1661 (1997).

The emollient(s) can be present in the present invention in an amount of greater than 0% to about 60%, relative to the total weight of the composition.

The makeup composition of the present invention may also contain particulate matter, i.e., fillers, to help give it a powder finish. These fillers may optionally be surface-treated or modified as known in the art. Useful fillers include, but are not limited to, talc; starch; kaolin; boron nitride; silica; TEFLON (tetrafluoroethylene fluorocarbon polymers) available from the DuPont Co.; zinc oxides; titanium oxides; precipitated calcium carbonate; and synthetic polymer powders, such as polyethylene, polyesters (e.g., polyethylene isophthalate or terephthalate) and polyamides (e.g., nylon such as nylon-12) in the form of particles having a size less than 50 μm and which possess absorbing properties so as to impart to the skin a velvety appearance. Examples of such synthetic polymer powders also include nylon particles sold under the tradename ORGASOL by Elf-Atochem; polymethyl silsesquioxane powder such as TOSPEARL, available from Toshiba; microporous microspheres made of lauryl methacrylate-ethylene glycol dimethacrylate copolymers and sold by Dow Corning under the name POLYTRAP; and microspheres of expanded vinylidene chloride, acrylonitrile and methacrylate terpolymer sold under the tradename EXPANCEL by Akzo-Nobel. Also useful as fillers are micas which are aluminosilicates of varied compositions, and which are provided in the form of flakes having a size ranging from 2 to 200 μm, preferably from 5 to 70 μm, and a thickness from 0.1 to 5 μm, preferably from 0.2 to 3 μm. The micas can be of natural origin, such as muscovite, margarite, rescolithe, lipidolithe, and biotite, or of synthetic origin. The micas are generally transparent and impart to the skin a satin aspect.

In addition, the makeup composition of the present invention may contain pigments and colorants which may be chosen from, but are not limited to:

mineral pigments, such as, for example: titanium dioxide (rutile or anatase) optionally surface treated and listed in the Color Index under reference Cl 77891; black, yellow, red and brown iron oxides listed in Color Index under references Cl 77499, 77492 and 77491; manganese violet (Cl 77742); ultramarine blue (Cl 77007); chromium oxide (Cl 77288); hydrated chromium oxide (Cl 77289); and ferric blue (Cl 77510);

organic pigments such as, for example, D & C Red No. 19 (Cl 45170); D & C Red No. 9 (Cl 15585); D & C Red No. 21 (Cl 45380); D & C Orange No. 4 (Cl 15510); D & C Orange No. 5 (Cl 45370); D & C Red No. 27 (Cl 45410); D & C Red No. 13 (Cl 15630); D & C Red No. 7 (Cl 15850:1); D & C Red No. 6 (Cl 15850:2); D & C Yellow No. 5 (Cl 19140); D & C Red No. 36 (Cl 12085); D & C Orange No. 10 (Cl 45475); D & C Yellow No. 6 (Cl 15985); D & C Red No. 30 (Cl 73360); D & C Red No. 3 (Cl 45430); carbon black (Cl 77766); and carmine lakes (Cl 75470);

nacreous pigments such as, for example, white nacreous pigments such as mica covered with titanium oxide and bismuth oxychloride; and colored nacreous pigments, such as titanium mica with iron oxides, titanium mica with ferric blue or chromium oxide, titanium mica with an organic pigment of the above-mentioned type, as well as those based on bismuth oxychloride.

The composition of the invention may also include any additive conventionally used in the cosmetics or dermatological field, such as, but not limited to antioxidants, fragrances, preservatives, thickeners, surfactants, cosmetic active principles, moisturizers, botanical extracts, vitamins, dyes, pigments, fillers, or sunscreens. With the inclusion of appropriate sunscreen agents, in one embodiment the invention can also be modified to produce an SPF effect.

The makeup product of the invention may be made by mixing all the ingredients together at a temperature ranging from 95° C. to 110° C. until the ingredients are melted.

The invention will be further clarified by the following examples, which are intended to be illustrative of the invention, but not limiting thereof.

EXAMPLE 1

(Inventive)

A makeup stick having the following composition was prepared. The result was a creamy, silky, stable product:

| | |
|---|---|
| Polyethylene Wax | 12.00% |
| Dimethicone Copolyol Beeswax | 3.00% |
| Skin-conditioning emollients | 55.50% |
| Pigments | 12.15% |
| Fillers | 16.85% |
| Preservatives | 0.50% |
| | 100.00% |

EXAMPLE 2

(Inventive)

A makeup stick having the following composition was prepared. The result was a creamy, stable product:

| | |
|---|---|
| Microcrystalline Wax | 3.500% |
| Polyethylene Wax | 9.000% |
| PEG-12 Carnauba Wax | 1.500% |
| Dimethicone Copolyol Beeswax | 1.500% |
| Skin-conditioning emollients | 55.00% |
| Pigments | 12.15% |
| Fillers | 16.85% |
| Preservatives | 0.50% |
| | 100.00% |

EXAMPLE 3

(Comparative)

The following composition was prepared. The waxes used were carnauba, candelilla, PEG-12 carnauba, and microcrystalline. Thus, only waxes from the "hard" category, that is, those having a penetration of 1 to 7.5 mm and a melting point of greater than 95° C., were used. No organically modified beeswax was used. The result was a product with a waxy, candle-stick like texture, illustrating that when the combination of waxes used is different from that of the present invention, an unsatisfactory product is obtained.

| | |
|---|---|
| Carnauba Wax | 4.00% |
| Candelilla Wax | 2.00% |
| PEG-12 Carnauba Wax | 1.00% |
| Microcrystalline Wax | 3.00% |
| Skin-conditioning emollients | 51.99% |
| Pigments | 9.05% |
| Fillers | 28.41% |
| Preservatives | 0.55% |
| | 100.00% |

It will be apparent to those skilled in the art that various modifications and variations can be made in the compositions of the invention without departing from the spirit or scope of the invention. Thus, it is intended that the present invention cover the modifications and variations of this invention provided that they come within the scope of the appended claims and their equivalents.

What is claimed is:

1. A composition which can be molded in the form of a stick or hot-poured, said composition comprising at least one polyethylene wax having a melting point of greater than 95° C. and a penetration of from 1 to 7.5 mm, and at least one organically modified beeswax having a penetration of greater than 7.5 mm.

2. A composition according to claim 1, wherein said at least one polyethylene wax having a melting point of greater than 95° C. and a penetration of from 1 to 7.5 mm has a weight-average molecular weight ranging from 350 to 900.

3. A composition according to claim 1, wherein said at least one polyethylene wax having a melting point of greater than 95° C. and a penetration of from 1 to 7.5 mm has a weight-average molecular weight ranging from 400 to 500.

4. A composition according to claim 1, wherein said at least one polyethylene wax having a melting point of greater than 95° C. and a penetration of from 1 to 7.5 mm is present in said composition in an amount ranging from greater than 0% to about 12% relative to the total weight of the composition.

5. A composition according to claim 1, wherein said at least one organically modified beeswax having a penetration greater than 7.5 mm is chosen from PEG-8 beeswax, polyglycerol-3 beeswax, and dimethicone copolyol beeswax.

6. A composition according to claim 5, wherein said at least one organically modified beeswax having a penetration greater than 7.5 mm is dimethicone copolyol beeswax.

7. A composition according to claim 1, wherein said at least one organically modified beeswax having a penetration greater than 7.5 mm is present in said composition in an amount ranging from greater than 0% to about 7% relative to the total weight of the composition.

8. A composition according to claim 1, further comprising at least one additional wax chosen from synthetic waxes having a penetration of greater than 7.5 mm and natural waxes which are non-modified and have a penetration of from 11 to 23 mm.

9. A composition according to claim 8, wherein said at least one additional wax is present in said composition in an amount ranging from greater than 0% to about 7% relative to the total weight of the composition.

10. A composition according to claim 9, wherein said synthetic waxes having a penetration of greater than 7.5 mm are chosen from microcrystalline, ozokerite, ceresine, hydrogenated jojoba, and paraffin waxes.

11. A composition according to claim 8, wherein said non-modified natural wax is a non-modified beeswax having a penetration of from 11 to 23 mm.

12. A composition according to claim 1, further comprising at least one skin conditioning emollient.

13. A composition according to claim 12, wherein said at least one emollient is chosen from fatty bodies liquid at ambient temperature.

14. A composition according to claim 13, wherein said fatty bodies liquid at ambient temperature are chosen from esters, mineral oils, animal oils, vegetable oil, synthetic oils, and silicone oils.

15. A composition according to claim 12, wherein said at least one emollient is present in the composition in an amount of greater than 0% to about 60% relative to the total weight of the composition.

16. A composition according to claim 1, further comprising at least one additive chosen from-antioxidants, fragrances, preservatives, thickeners, surfactants, cosmetic active principles, moisturizers, botanical extracts, vitamins, dyes, pigments, fillers, and sunscreens.

17. A process for caring for and/or for making up skin, eyelids, or lips comprising applying to said skin, eyelids, or lips a composition which can be molded in the form of a stick or hot-poured, said composition comprising at least one polyethylene wax having a melting point of greater than 95° C. and a penetration of from 1 to 7.5 mm, and at least one organically modified beeswax having a penetration of greater than 7.5 mm.

18. A composition according to claim 1, wherein said composition is in the form of a make-up stick, a concealer stick, an eyeshadow stick, an eyeliner stick, a blush stick, a lipstick, or a hot-poured product.

19. A composition according to claim 1, wherein said composition is anhydrous.

* * * * *

UNITED STATES PATENT AND TRADEMARK OFFICE
CERTIFICATE OF CORRECTION

PATENT NO.   : 6,503,516 B1
DATED        : January 7, 2003
INVENTOR(S)  : Terry Van Liew, Olga Alonzo and Michael Smith It is certified that error appears in the above-identified patent and that said Letters Patent is hereby corrected as shown below:

<u>Column 5,</u>
Line 39, "claim 9" should read -- claim 8 --.

<u>Column 6,</u>
Line 20, "from-antioxidants" should read -- from antioxidants --.

Signed and Sealed this

Fifteenth Day of April, 2003

JAMES E. ROGAN
*Director of the United States Patent and Trademark Office*